(12) United States Patent
Pantchenko

(10) Patent No.: US 9,244,440 B2
(45) Date of Patent: Jan. 26, 2016

(54) TEMPERATURE DEPENDENT DEVICE

(71) Applicant: Oxana S Pantchenko, Scotts Valley, CA (US)

(72) Inventor: Oxana S Pantchenko, Scotts Valley, CA (US)

( * ) Notice: Subject to any disclaimer, the term of this patent is extended or adjusted under 35 U.S.C. 154(b) by 0 days.

(21) Appl. No.: 14/616,680

(22) Filed: Feb. 7, 2015

(65) Prior Publication Data

US 2015/0153239 A1 Jun. 4, 2015

Related U.S. Application Data

(60) Provisional application No. 62/123,463, filed on Nov. 19, 2014.

(51) Int. Cl.
*G01K 3/00* (2006.01)
*G04F 3/06* (2006.01)
*G01N 33/04* (2006.01)
*G01K 1/02* (2006.01)
*G01K 3/04* (2006.01)

(52) U.S. Cl.
CPC .. *G04F 3/06* (2013.01); *G01K 1/02* (2013.01); *G01K 3/04* (2013.01); *G01N 33/04* (2013.01); *G01K 2207/04* (2013.01)

(58) Field of Classification Search
USPC .................................. 374/102, 141; 116/216
See application file for complete search history.

(56) References Cited

U.S. PATENT DOCUMENTS

| | | | |
|---|---|---|---|
| 6,580,662 B2 | 6/2003 | Vassallo | |
| 7,061,832 B1 | 6/2006 | Lansing | |
| 7,522,477 B1 | 4/2009 | Sheldon | |
| D668,972 S | 10/2012 | Solly et al. | |
| 8,441,893 B2 | 5/2013 | Stephens Stauffer et al. | |
| 2003/0069796 A1* | 4/2003 | Elwood et al. | 705/23 |
| 2003/0198135 A1 | 10/2003 | Beatty et al. | |
| 2007/0014327 A1* | 1/2007 | Faiola | 374/102 |
| 2008/0031302 A1* | 2/2008 | Rund et al. | 374/102 |
| 2008/0279724 A1* | 11/2008 | Dicarlo | 422/58 |
| 2014/0132240 A1 | 5/2014 | McQuirk et al. | |

* cited by examiner

*Primary Examiner* — Mirellys Jagan

(57) ABSTRACT

The present disclosure relates generally to a temperature dependent device. Embodiments of the invention provide information regarding the useful life of perishable goods.

18 Claims, 2 Drawing Sheets

TEMPERATURE DEPENDENT DEVICE

PRIORITY OF INVENTION

Figure 1:
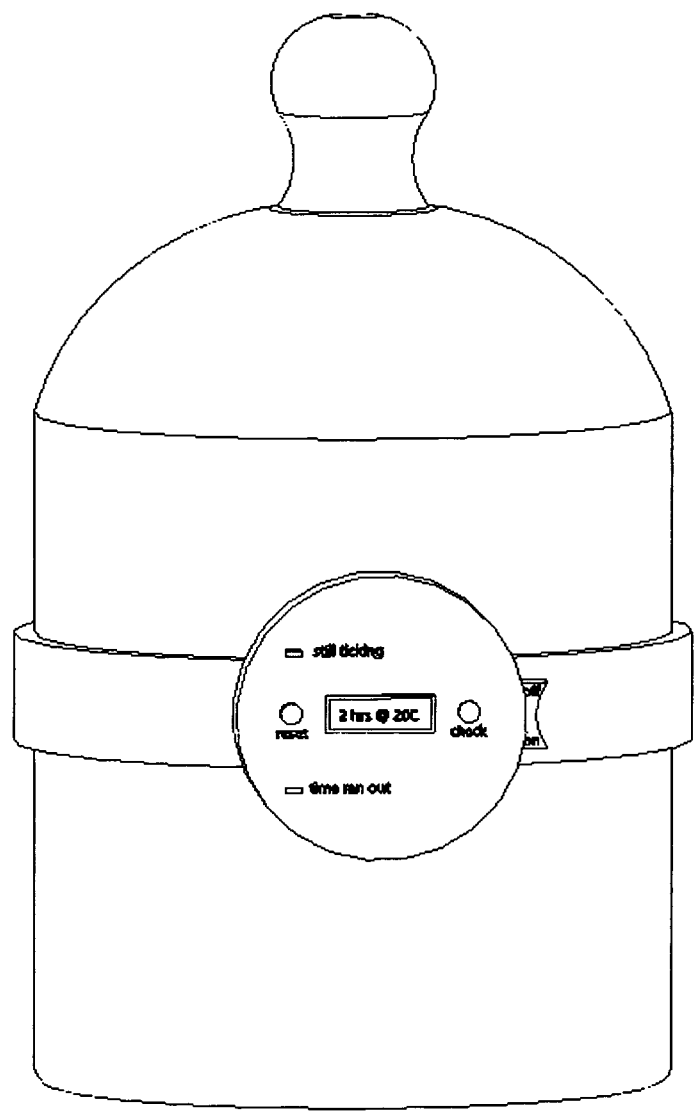

This application claims the benefit of priority under 35 U.S.C. §119(e) to U.S. Provisional Patent Application Ser. No. 62/123,463, filed Nov. 19, 2014. The entirety of the Provisional Application listed above is incorporated herein by reference.

FIELD OF THE INVENTION

This invention relates generally to a temperature dependent device and its use in indicating the useful life of perishable goods.

BACKGROUND OF THE INVENTION

Improving the useful life of perishable goods has been a focus of research for many years. Advancements in the ability to store perishable goods have prolonged the useful life of perishable goods. However, storage of a perishable good does not exclusively determine the duration of the perishable good's useful life. Exposure to temperatures can increase or decrease a perishable good's useful life. A perishable good, such as human breast milk, will expire quicker in higher temperatures than in low temperatures. Even though modern storage containers provide the ability to store a perishable good for an extended period of time, there is a need to determine whether the stored perishable good's useful life remains.

Information relevant to attempts to address this problem can be found in U.S. Pat. Nos. 6,580,662 and 7,061,832.

There remains a need to manage the useful life of perishable goods by: accounting for multiple temperature differences over the duration of the useful life of a perishable good, preventing uncertainty in differentiating and distinguishing perishable goods stored at different times, minimizing wasteful discarding of perishable goods, alerting of temperatures contributing to a rapid expiration, and providing a versatile device capable of accompany a container and tracking the useful life of the perishable goods of the container.

SUMMARY OF THE INVENTION

Managing the useful life of a perishable good can be achieved by monitoring the temperature at which perishable goods are stored. The present invention provides a temperature dependent device possessing the utility of monitoring the temperature and duration at which perishable goods are stored as set forth below. The perishable goods may include, but are not limited to human breast milk, toddler formula, milk, liquid and food.

DESCRIPTION

Reference will now be made in detail to certain claims of the invention, examples of which are illustrated in the accompanying figures. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims. For examples, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference herein to a method comprising two or more defined steps, the defined steps can be carried in any order or simultaneously (except where the context excludes that possibility), and the method can include one or more other steps which are carried out before any of the defined steps, between two of the defined steps, or after all the defined steps (except where the context excludes that possibility).

Definitions

Unless stated otherwise, the following terms and phrases as used herein are intended to have the following meanings:

"Alarm" refers to an alert. Non-limiting examples of an alarm include a sound, a vibration, and a light.

"Comprises" and grammatical equivalents thereof are used herein to mean that other components are optionally present. For example, an article "comprising" components A, B, and C can consist of components A, B, and C or can contain not only components A, B, and C, but also one or more other components.

"Band" refers to a means of affixing the temperature dependent device to another object.

"Check button" refers to a button on the temperature dependent device that performs an action when pressed.

"Container" refers to a storing entity. Non-limiting examples of a container include a baby bottle, a pouch, a bag and a box. The container may be sealed or unsealed.

"Corresponding" refers to a relationship between a measured temperature and a time interval.

"Display" refers to a medium where a value can be shown. A non-limiting example of a display includes a touch screen display.

"Expiration time" refers to when the useful life as defined below expires.

"Expires" refers to a date in which a perishable good is no longer healthy to eat.

"Flexible" refers to any non-rigid property. Something "flexible" is capable of bending.

"Food" refers to an edible substance.

"Indicator" refers to any means of indicating a status of the temperature dependent device. Non-limiting examples of an indicator include LEDs, alarms, and lights.

"Initial Value" refers to a time or number indicating a starting point from which to add or subtract values.

"Liquid" refers to a substance that is safe to drink.

"Looks Up" refers to a microcontroller or a microprocessor performing a program.

"Milk" refers to animal milk and milk substitutes. Non-limited examples of milk substitutes include soy milk, almond milk, and coconut milk.

"Perishable good" refers to any food, drink or combination thereof. Non-limiting examples of perishable goods include human breast milk, toddler formula, milk, liquid and food.

"Resulting value" refers to the combination of an initial value and time interval.

"Suction cup" refers to a cup-shaped device in which a partial vacuum can be produced when applied to a surface. A suction cup can be made of a multitude of materials. A non-limiting list of materials includes rubber, glass and plastic.

"Thermometer" refers to a device capable of measuring temperature.

"Time interval" refers to a specific amount of time allotted to a particular temperature.

"Timer" refers to a component capable of measuring time. A non-limiting example of a timer is included in a programmed microcontroller.

"Useful life" refers to any period of time during which an edible substance may be safely consumed.

DETAILED DESCRIPTION OF THE ELEMENTS

Specific depictions as well as specific embodiments of the invention described herein are for illustration only; they do not exclude other configurations.

In one specific embodiment of the invention, a temperature dependent device comprises a thermometer and a timer wherein:
  the thermometer takes a temperature reading;
  the temperature dependent device looks up a time interval corresponding to the temperature reading;
  a remaining useful life is computed using the time interval; and
  the thermometer continues taking temperature readings until the remaining useful life expires.

In another specific embodiment of the invention, a temperature dependent device comprises a thermometer, a timer, and a display wherein:
  the thermometer takes a temperature reading;
  the temperature dependent device looks up a time interval corresponding to the temperature reading;
  a remaining useful life is computed using the time interval;
  a value is shown on the display; and
  the thermometer continues taking temperature readings until the remaining useful life expires.

In another specific embodiment of the invention, a temperature dependent device comprises a thermometer, a timer, a display, a check button, an on/off switch, and a band; wherein:
  the on/off switch is set in an "on" position;
  the thermometer takes a temperature reading;
  the temperature dependent device looks up a time interval corresponding to the temperature reading;
  a remaining useful life is computed using the time interval;
  a value is shown on the display wherein the check button is pressed to show another value on the display; and
  the thermometer continues taking temperature readings until the remaining useful life expires.

In another specific embodiment of the invention, a temperature dependent device comprises a thermometer, a timer, a display, a check button, an on/off switch, a band, and an indicator; wherein:
  the on/off switch is set in an "on" position;
  the temperature dependent device looks up a time interval corresponding to the temperature reading;
  a remaining useful life is computed using the time interval;
  a value is shown on the display wherein the check button is pressed to show another value on the display;
  a first indicator is on;
  the thermometer continues taking temperature readings until the remaining useful life expires; and
  the first indicator is off and a second indicator is on.

In one specific embodiment of the invention, the thermometer is a precision temperature monitoring device.

In one specific embodiment of invention, the timer is a microcontroller or a microprocessor.

In one specific embodiment of the invention the display shows values. Non-limiting examples of the values include remaining useful life, current temperature, current time, current date, expiration time, and expiration date. The values can be shown at the same time on a single display. The values can also been shown at the same time on multiple displays. The values can also be shown individually wherein a single value is shown until the check button is pressed, which would change the shown value to a different value.

In one specific embodiment of the invention, the useful life is computed wherein:
  the time interval that corresponds to the temperature reading is deducted from an initial value wherein:
    the initial value is a maximum value.

In another specific embodiment of the invention, the useful life is computed wherein:
  the time interval that corresponds to the temperature reading is added to an initial value wherein:
    the initial value is a minimum value.

In one specific embodiment of the invention, the time interval comprises a milk storage guidance published by the Centers for Disease Control and Preventions, *Storage Duration of Fresh Human Milk for Use with Healthy Full Term Infants* as interpreted by Table I. Table I shows an interpretation of a temperature reading versus.

TABLE I

| Location | Temperature | Duration | Comments |
| --- | --- | --- | --- |
| Countertop, table | Room temperature (up to 77° F. or 25° C.) | 6-8 hours | Containers should be covered and kept as cool as possible; covering the container with a cool towel may keep milk cooler. |
| Insulated cooler bag | 5-39° F. or −15-4° C. | 24 hours | Keep ice packs in contact with milk containers at all times, limit opening cooler bag. |
| Refrigerator | 39° F. or 4° C. | 5 days | Store milk in the back of the main body of the refrigerator. |
| Freezer | | | |
| Freezer compartment of a refrigerator | 5° F. or −15° C. | 2 weeks | Store milk toward the back of the freezer, where temperature is most constant. Milk stored for longer durations in the ranges listed is safe, but some of the lipids in the milk undergo degration resulting in lower quality. |
| Freezer compartment of refrigerator with separate doors | 0° F. or −18° C. | 3-6 months | |
| Chest or upright deep freezer | −4° F. or −20° C. | 6-12 months | |

TABLE I-continued

| Location | Temperature | Duration | Comments |
| --- | --- | --- | --- |

Reference: Academy of Breastfeeding Medicine. (2004) *Clinical Protocol Number # 8: Human Milk Storage Information for Home Use for Healthy Full Term Infants* [PDF-125k]. Princeton Junction, New Jersey: Academy of Breastfeeding Medicine. Available In one specific embodiment of the invention, the indicators are green and red LEDs wherein:
the green LED indicates there is remaining useful life; an the red LED indicates that the useful life has expired.

In one specific embodiment of the invention, the band is affixed to a container. It is within the scope of the invention that the band is made of flexible or ridged material. The band may also contain a designated area for a user to write information such as a name or date.

In another specific embodiment of the invention, the band is replaced by suction cups.

In one specific embodiment of the invention, the temperature dependent device described herein can be used with containers comprising perishable goods. Non-limiting examples of perishable goods include human breast milk, toddler formula, milk, liquid and food. It is a preferred embodiment that the device is affixed to or fitted around the container.

The device described herein may be used in a method for determining the useful life of a perishable good. The device may further be used in a method for accounting for multiple temperature changes over the duration of a useful life of perishable goods. The device may further be used in a method of alerting a caretaker if milk is stored at too high of a temperature.

In one specific embodiment of the invention, a temperature dependent device comprises a thermometer and an alarm, wherein:
the thermometer takes a temperature reading;
the temperature dependent device senses a temperature or a change on temperature; and
the alarm is triggered by the temperature or change in temperature.

In another specific embodiment of the invention, a temperature dependent device comprises a thermometer, an alarm and a display wherein:
the thermometer takes a temperature reading;
the temperature dependent device senses a temperature or a change on temperature;
the alarm is triggered by the temperature or change in temperature; and
a value is shown on the display.

In another specific embodiment of the invention, a temperature dependent device comprises a thermometer, an alarm, a display, and a flexible band wherein:
the thermometer takes a temperature reading;
the temperature dependent device senses a temperature or a change on temperature;
the alarm is triggered by the temperature or change in temperature; and a value is shown on the display.

In one specific embodiment of the invention, a temperature dependent device comprises a thermometer, a timer and an alarm, wherein:
the thermometer takes a temperature reading;
the temperature dependent device senses a temperature or a change in temperature;
the timer is triggered; and
the alarm is triggered by the timer In another specific embodiment of the invention, a temperature dependent device comprises a thermometer, a timer, an alarm, and a display, wherein:
the thermometer takes a temperature reading;
the temperature dependent device senses a temperature or a change in temperature;
the timer is triggered;
the alarm is triggered by the timer; and
a value is shown on the display.

In another specific embodiment of the invention, a temperature dependent device comprises a thermometer, a timer, an alarm, a display, and a flexible band, wherein:
the thermometer takes a temperature reading;
the temperature dependent device senses a temperature or a change in temperature;
the timer is triggered;
the alarm is triggered by the timer; and
a value is shown on the display.

Figure 2:
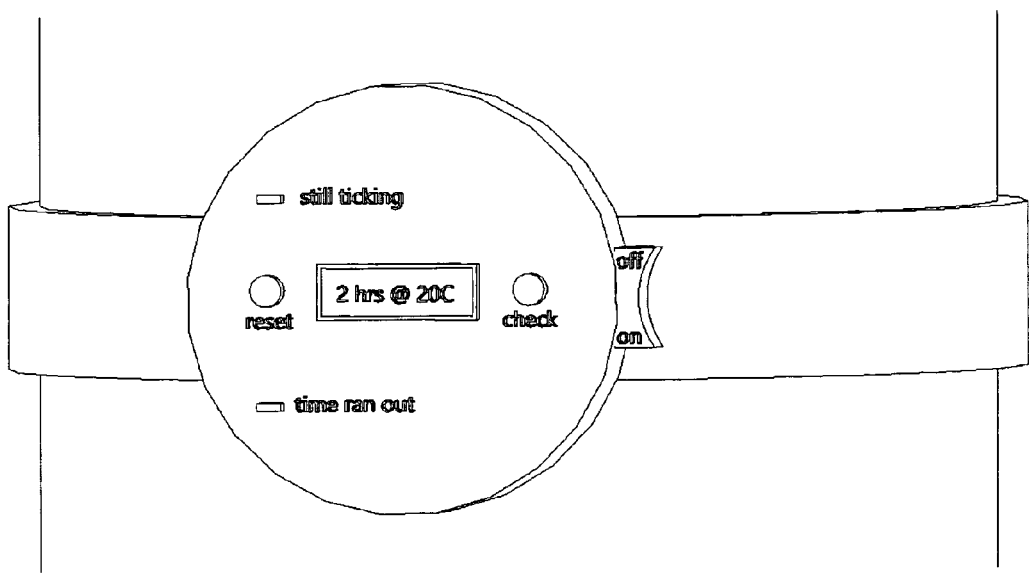

Specific embodiments of the invention include FIG. 1 and FIG. 2. In the specific embodiment depicted by FIG. 1, the temperature dependent device is attached to a baby bottle. In the specific embodiment depicted by FIG. 2, the temperature dependent device is shown with a configuration of some elements of the invention.

The device described herein presents many advantages, including accounting for multiple temperature differences over the duration of the useful life of a perishable good, preventing uncertainty in differentiating and distinguishing perishable goods stored at different times, minimizing wasteful discarding of perishable goods, alerting of temperatures contributing to a rapid expiration, and providing a versatile device capable of accompany a container and tracking the useful life of the perishable goods of the container.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following Claims. It is apparent that certain modifications of the methods and compositions of the following Claims can be made within the scope and spirit of the invention.

What is claimed is:

1. A device comprising a microprocessor and a thermometer wherein:
 (a) the microprocessor sets an initial value, wherein the initial value is a maximum value;
 (b) the thermometer measures a temperature;
 (c) the microprocessor reads the measured temperature from the thermometer;
 (d) the microprocessor looks up a time interval corresponding to the measured temperature;
 (e) the microprocessor calculates a resulting value by subtracting the time interval from the initial value wherein
  (I) if the resulting value matches a useful life value, then the microprocessor triggers a first indicator; or (II) if the resulting value does not match the useful life value, then the microprocessor triggers a second indicator and repeats (b), (c), (d), and (e).

2. The device of claim 1 further comprising a display, check button, an on/off switch, and a band wherein a value is shown on the display wherein the check button is pressed to show another value on the display.

3. The device of claim 1 used to determine the useful life of a perishable good.

4. The device in claim 1 further comprising a display.

5. The device of claim 4 wherein the display shows at least one value selected from the group consisting of remaining useful life, current temperature, current time, current date, expiration time, expiration date, and time since expiration.

6. The device of claim 1 further comprising a means of affixation to a container selected from the group consisting of a band and suction cups.

7. The device of claim 6 wherein the container is selected from the group consisting of a baby bottle, a pouch, a bag, and a box.

8. The device of claim 1 wherein the time interval is specific to a perishable good.

9. The device of claim 8 wherein perishable good is selected from the group consisting of human breast milk, toddler formula and milk.

10. A device comprising a microprocessor and a thermometer wherein:
   (a) the microprocessor sets an initial value, wherein the initial value is a minimum value;
   (b) the thermometer measures a temperature;
   (c) the microprocessor reads the measured temperature from the thermometer;
   (d) the microprocessor looks up a time interval corresponding to the measured temperature;
   (e) the microprocessor calculates a resulting value by adding the time interval to the initial value wherein
      (I) if the resulting value matches a useful life value, then the microprocessor triggers a first indicator; or
      (II) if the resulting value does not match the useful life value, then the microprocessor triggers a second indicator and repeats (b), (c), (d), and (e).

11. The device of claim 10 further comprising a display, check button, an on/off switch, and a band wherein a value is shown on the display wherein the check button is pressed to show another value on the display.

12. The device of claim 10 used to determine the useful life of a perishable good.

13. The device in claim 10 further comprising a display.

14. The device of claim 13 wherein the display shows at least one value selected from the group consisting of remaining useful life, current temperature, current time, current date, expiration time, expiration date, and time since expiration.

15. The device of claim 10 further comprising a means of affixation to a container selected from the group consisting of a band and suction cups.

16. The device of claim 15 wherein the container is selected from the group consisting of a baby bottle, a pouch, a bag, and a box.

17. The device of claim 10 wherein the time interval is specific to a perishable good.

18. The device of claim 17 wherein perishable good is selected from the group consisting of human breast milk, toddler formula and milk.

\* \* \* \* \*